United States Patent [19]

Lee

[11] 4,083,931

[45] Apr. 11, 1978

[54] PROCESS FOR TREATING ALDOL-CONDENSATION POLYOL WASTE LIQUOR

[75] Inventor: Fu-Ming Lee, Toledo, Ohio

[73] Assignee: Industrial Sales and Factoring Corporation, Toledo, Ohio

[21] Appl. No.: 716,555

[22] Filed: Aug. 23, 1976

[51] Int. Cl.² .................... C07C 29/24; C07C 53/08; C01D 15/06
[52] U.S. Cl. .................................. 423/199; 560/248; 260/542; 260/637 P; 260/637 P; 423/551
[58] Field of Search ............. 423/193, 199, 551; 260/499, 542, 561 R, 583 N, 583 R, 583 P, 527 R, 616, 635 P, 637 R, 637 P, 643 R, 643 A, 701, 703, 705

[56] References Cited

U.S. PATENT DOCUMENTS

| | | | |
|---|---|---|---|
| 1,039,875 | 10/1912 | Wolff | 260/488 F |
| 2,407,920 | 9/1946 | Cox | 260/488 F |
| 2,433,323 | 12/1947 | Reiter | 260/499 |
| 3,357,899 | 12/1967 | Robeson | 250/542 |
| 3,578,703 | 5/1971 | Schoenbrunn et al. | 260/488 F |

FOREIGN PATENT DOCUMENTS

| | | | |
|---|---|---|---|
| 2,465 of | 1913 | United Kingdom | 260/499 |
| 349,678 | 9/1972 | U.S.S.R. | 260/488 F |
| 345,128 | 8/1972 | U.S.S.R. | 260/542 |

*Primary Examiner*—O. R. Vertiz
*Assistant Examiner*—Gary P. Straub

[57] ABSTRACT

A process for treating and recovering components from aldol-condensation polyol waste liquor containing sodium formate, water, polyol, and organic by-products comprising A. vacuum crystallizing and removing sodium formate; B. introducing methanol and sulfuric acid; C. distilling to remove and recover methyl formate; D. increasing the pH to about 6.5 to 7.0; E. cooling to precipitate Glauber's salt, polyol and organics; and F. adding water to dissolve and separate the Glauber's salt and recover substantially pure polyol and organics.

2 Claims, No Drawings

PROCESS FOR TREATING ALDOL-CONDENSATION POLYOL WASTE LIQUOR

BACKGROUND OF THE INVENTION

A. Field of the Invention

This invention relates to a process for treating aldol-condensation polyol waste liquor.

B. Description of the Prior Art

It is well known that aldol-condensation polyol waste liquors contain sodium formate, polyol, water and organic by-products. Generally, this waste liquor is disposed of. However, due to ecological reasons, disposing of such waste liquors can be a problem. Robeson, U.S. Pat. No. 3,357,899 of Dec. 12, 1967, has proposed a process for treating such waste liquor involving acidifying to convert the sodium formate to sodium sulfate and formic acid. The sodium sulfate is removed as a solid, and the formic acid is removed as an azeotrope with water. The polyol is not recoverable in Robeson's process since it is contaminated with formic acid, and the formic acid is only recoverable in the form of an azeotrope. Thus Robeson's process is uneconomical and impracticable.

Other methods of treating aldol-condensation waste liquors are disclosed by Leonard, U.S. Pat. No. 3,179,704, involving extraction with dimethyl formamide; Snow et al, U.S. Pat. No. 2,441,602 involving extraction of the organics with ethanol; Clunie et al., U.S. Pat. No. 3,066,171, involving ozone treatment; and McGrath, U.S. Pat. No. 2,690,993, involving azeotropic distillation with water. All of these processes suffer from one or more disadvantage as compared with the process of the invention.

A need exists for an economical and practical process which results in recoverable, separated products which have sufficient value to counter-balance the waste liquor treatment costs.

SUMMARY OF THE INVENTION

It is an object of the present invention to provide a process for treating aldol-condensation waste liquor which results in recoverable, separated products which have substantial value.

It is a further object to provide a process for treating aldol-condensation waste liquor which substantially eliminates waste disposal problems.

A still further object of the present invention is to provide an ecological and economical process for treating pentaerithritol waste liquor.

These and other objects, as will become apparent from the following disclosure, are achieved by the present invention which comprises, on an overall basis, adding relatively inexpensive sulfuric acid and methanol, and recovering valuable methyl formate, sodium sulfate, sodium formate, and polyol.

DETAILED DESCRIPTION OF THE INVENTION AND THE PREFERRED EMBODIMENTS

Typical polyols which are produced by aldol condensation are trimethylolethane, trimethylol propane, pentaerithritol and anhydroenneaheptital.

These polyols are conventionally produced by the condensation of aldehydes, for example, acetaldehyde with formaldehyde to make pentaerithritol, in an aqueous medium containing a condensation catalyst, usually alkali metal and alkaline earth metal compounds. See, for example, Mitchell et al., U.S. Pat. No. 2,790,836. The polyol product is generally recovered by fractional crystallization, but there results from the fractional crystallization a waste liquor which contains larger quantities of alkali metal formate (about 25–35%), organic by-products including polymers of the polyol and formals of the polyol (about 2 to 12%), unrecovered polyol product (about 4 to 10%), and the balance water.

In carrying out the process of the invention, it is preferred to first evaporate some of the water out of the waste liquor so that the resultant water content is about 40 to 60 weight percent. One suitable method of evaporating water out is to use a vacuum in a forced circulating evaporator at about 80° to 90° C. A suitable vacuum pressure is about 20 inches of mercury.

The waste liquor is introduced into a vacuum crystallizer and sodium formate is removed as a substantially pure solid. Preferably a temperature of about 35° to 50° C. is maintained in the crystallizer. It is also preferred to recycle the suspension liquor from the crystallizer to mix with fresh feed to improve sodium formate crystal size. The vacuum crystallizer used is preferably one which operates on a continuous feed basis. The resultant technical grade sodium formate is preferably removed by centrifuge, and about 40 to 60% of the sodium formate in the waste liquor can be removed by this step.

The final mother liquor from the preceeding step is then preferably cooled to about 10° to 15° C. and is mixed with excess methanol, based on the sodium formate content of the final mother liquid being treated. About 2.5 times the stochiometric amount of methanol has been found to be suitable and efficient.

Either simultaneous with, or subsequent to, the methanol addition, a slight excess amount of strong inorganic acid, preferably concentrated sulfuric acid, is added to the mixture at such a rate so as to maintain the temperature of the mixture below about 30° C. as to minimize evaporation of the methyl formate being formed. Carbon monoxide evolution is avoided because the sulfuric acid is added to a dilute aqueous solution under controlled temperature. The excess of methanol, along with sufficient mixing, helps to prevent flashing during the acid addition.

Next, mild distillation to remove methyl formate which is the esterification reaction product between the methanol and formic acid is carried out. Atmospheric pressure batch distillation is suitable for this step since methyl formate does not form an azeotrope with water and methanol, and the boiling point of methyl formate is only 31.5° C. The distillation of the methyl formate is suitably carried out at about 30° to 100° C.

Surprisingly low energy consumption is needed for the distillation of the methyl formate because of the low boiling points of methanol and methyl formate. Also, the hydroxyl groups of the polyol are unattacked by the formic acid.

Preferably the distillation of the methyl formate is carried out in two steps, the second distillation step being for separation of the methyl formate and methanol which distill over together in the first distillation. When two steps are used, the methyl formate can be recovered in very high yields and substantially 100% purity.

The bottom residue of the second distillation generally contains less than 10 weight percent methyl formate, over 70 weight percent methanol, and the balance water, but this residue can be recycled to act as part of the methanol feed in the previous step. Thus, the overall yield of methyl formate can be as high as 98 percent. Surprisingly no formic acid is left in the bottom residue of the first distillation of this step.

The next step involves neutralization with base. Preferably enough sodium hydroxide is introduced to the bottom residue of the first distillation of the previous step to increase the pH to about 6.5 to 7.0.

Next, Glauber's salt, $Na_2SO_4.10H_2O$, is formed by gradual cooling to below about 25° C., and because almost all of the water is absorbed by the formation of the Glauber's salt, the Glauber's salt and the organics, including polyol, simultaneously precipitate without the need for an evaporation step, thus conserving significant energy.

Preferably, the mother liquor from this crystallization step is maintained at a low temperature, usually around 5° C., and is allowed to stand so as to cause further precipitation, the precipitate being combined with the major precipitate in the last step, and the mother liquor can be concentrated and used in the manufacture of synthetic lubricants.

The solids, containing Glauber's salt and the major part of the organics and polyol, is separated by adding enough water at the temperature to dissolve sodium sulfate but not the organics or polyol. The amount of water needed is calculated based on the fact that the Glauber's salt will contribute 10 moles of water per mole of sodium sulfate.

The resultant sodium sulfate solution is separated from the organics, preferably by vacuum drum filtering at about 40° C., although other suitable methods of separation can also be used. The sodium sulfate solution is then cooled to form Glauber's salt again, and substantially pure sodium sulfate can thus be obtained.

The solids remaining after the first Glauber's salt dissolution step are polyol with small amounts of organics. For example, when the polyol is pentaerithritol, the polyol-organics solids can be sold as technical pentaerithritol since typically over 90 mole % is pentaerithritol and the sodium sulfate and other inorganic content is non-detectable.

The great advantage of the novel process of the invention is that it allows a self-contained process with very low energy and water consumption and very high yields of polyol, methyl formate, sodium formate, and sodium sulfate, the value of which can easily compensate for the costs of treating the waste liquor with the benefit of eliminating waste disposal problems.

The following example is presented to illustrate one embodiment of the invention, but it should be understood, of course, that the invention is not limited to this single embodiment.

EXAMPLE

A. About 300 gallons of technical pentaerithritol (PE) waste liquor having the composition specified in Table I was fed continuously to a forced circulating evaporator to concentrate the liquor from 40 to 60 weight percent solids under 20 inches mercury vacuum and 90° C. This concentrated liquor was then stored in a feed tank kept at 95° C. and used as the feed stock for a vacuum crystallizer.

TABLE 1

| COMPONENT | ANALYSIS OF TECH. PE WASTE LIQUOR, Wt. % |
|---|---|
| Sodium formate | 31.0 |
| PE | 6.5 |
| Di-PE | 0.7 |
| Water | 60.0 |
| Others* | 1.8 |

*These may include poly-PE, linear and cyclic PE formals.

The feed rate to the vacuum crystallizer was about 3 gallons per hour to maintain the retention time in the crystallizer to be about 6.5 hours. Steam jets were used to create the necessary vacuum so that the crystallizer temperature was kept at 35° to 40° C., depending upon the weight ratio between organics and sodium formate. In order to improve the crystal size distribution, fines were recirculated at a rate of 10 gallons per minute to mix with the fresh feed. The slurry from the crystallizer was transferred to a centrifuge kept at 35° to 40° C. for the separation. About 7.35 pounds per hour of sodium formate dry crystals were produced. 97.6 weight percent of the crystals were above 100 U.S. standard mesh screen in size. The mother liquor from the centrifuge was recycled to mix with the fresh feed to the evaporator for more passes until the weight ratio between organics and sodium formate was higher than 0.4. The yield per pass for the sodium formate process was found to be around 21 to 25%.

B. A portion of the final mother liquor from Step A (2002 gm. or 1528 ml. at 23° C.) was used as the feedstock to produce methyl formate, organics, and sodium sulfate. The analysis of this feedstock is given in Table 2.

TABLE 2

| COMPONENT | WT. PERCENT |
|---|---|
| PE | 14.7 |
| Di-PE | 2.2 |
| Linear PE formal | 0.3 |
| Cyclic PE formal | 0.1 |
| Other organics (Poly PE and poly PE formals) | 0.5 |
| Sodium formate | 34.7 |
| Water | 47.5 |

It was cooled to about 10° to 15° C. and 819 gm. of methyl alcohol was added with sufficient mixing. Next, 511 gm. of 98% concentrated sulfuric acid was slowly added with cooling applied, to remove the heat of mixing, to maintain the temperature below 30° C. The amount of added methyl alcohol was equivalent to 250 mole percent of the sodium formate found by analysis of the feedstock, while the amount of sulfuric acid added corresponds to 100 mole percent of sodium formate in the aforementioned feed. After sulfuric acid addition, the mixture was found having 13.6 weight percent free acid and a pH of 2.38. About 30 gm. of additional 98% sulfuric acid was added to bring the pH to 0.98 to warrant enough excess sulfuric acid presented as the catalyst for the esterification reaction between formic acid and methyl alcohol in the next distillation step.

C. The product of Step B was charged to a distillation flask equipped with a Goodloe packed column with 25 mm packing diameter and 24 inches packing depth (equivalent to 14-15 theoretical plates at the half flood point). The distillation was conducted at atmospheric pressure without reflux. The mixture started boiling at about 55° C. and its boiling point increased gradually up to 102° C. before the distillation was discontinued.

There was obtained 1156 gm. distillate containing 40.2 weight percent methyl alcohol, 49.1 weight percent methyl formate, and 10.7 weight percent of others (primarily water). In order to minimize the loss of methyl formate due to evaporation, the distillation receiver was maintained at 5° C. during the operation.

The distillate from the first (crude) distillation was transferred to another flask equipped with the Goodloe packed column and a distillation head, for the second distillation for separation of methyl formate, The distillation started with total reflux until the head temperature stabilized at 30.5° C., and then proceeded with 1:1 reflux ratio. About 576 gm. of 98.6 weight percent of methyl formate was produced as distillate, at 92.7% yield based upon theoretical expected value. This distillation step was repeated with 2:1 reflux ratio, and the corresponding distillate was 565 gm. of 100.0 weight percent methyl formate. The bottom residue weighed 580 gm. containing 6.6 weight percent methyl formate, 79.6 weight percent methyl alcohol, 0.6 weight percent formic acid, and the balance water. Based on material balance, 491 gm. of theoretical amount of the unreacted methyl alcohol should be recovered in the bottom residue of this second distillation, while the experimental result indicates 461.7 gm. was collected. Therefore, the recovery of unreacted methyl alcohol was found to be 94.0% based on the theoretical expected value.

D. 2240 gm. of residue from the first (crude) distillation, containing 1.7 weight percent free acid (primarily sulfuric acid), was reacted with 27.8 gm. of 50% sodium hydroxide aqueous solution to increase in the pH from 1.6 to 6.8.

E. The neutralized residue was cooled to 12° C. in 75 minutes under sufficient mixing. Due to the formation of Glauber's salt, the residue became very viscous in the latter part of the cooling process, so that a heavy duty, slow speed agitator was used for the mixing. After the slurry was separated by using a laboratory centrifuge, the solid mixture and filtrate weighed 1914 gm. and 354 gm., respectively. The filtrate was cooled at 5° C. for 18 hours for the further recovery of solids. The wet sulfate and organic cake weighed 45.5 gm. and was added back to the previous crude sulfate cake, after 309 gm. of final mother liquor was removed. Analysis of this final mother liquor showed 28.2 weight percent solids and non-detectable sulfate impurity.

F. The extracted wet solids from Step E is redissolved by adding 715 gm. of water to the wet solids (200 gm. or 17 weight percent of water in excess was used to ensure the complete dissolution of sodium sulfate). The dissolution process was carried out at 35° C. for about 1 hour before the organic cake was filtered out in a heated Buchner funnel at 35° C. This organic cake was then washed with 300 gm. of water at 37° C. while still in the Buchner funnel, to remove the final trace amount of sodium sulfate in the organics. The organic cake wash was recycled to the 35° C. warm water tank as make-up water for dissolving the crude sulfate cake in Step G. The amount of organics collected was 167.4 gm. (dry basis) containing only 0.28% of sodium sulfate. GC analysis of this cake is given in Table 3.

TABLE 3

| COMPONENT | MOLE % |
|---|---|
| PE | 91.1 |
| Di-PE | 8.1 |
| Linear PE formal | 0.6 |

TABLE 3-continued

| COMPONENT | MOLE % |
|---|---|
| Cyclic PE formal | 0.2 |

G. The sodium sulfate mother liquor from Step F was again cooled to 15° C. in an hour to allow Glauber's salt to crystallize under sufficient mixing. After the heavy hydrated slurry was separated in a centrifuge, 1398.6 gm. of wet Glauber's salt was collected (or 586.7 gm. dry sodium sulfate) with 99.4 weight percent purity. The amount of mother liquor collected from centrifuging was 950 gm. containing 9.4 weight percent sodium sulfate, 7.9 weight percent organics and 82.7 weight percent water. For further recovery of the solids, 641 gm. of water originally presented in the mother liquor, was evaporated to increase the concentration up to 50 weight percent solids, and the concentrated liquor was cooled at 5° C. for 5 hours. Additional 241 gm. of wet solids was recovered and was transferred to the 35° C. warm water tank for redissolving. The final mother liquor was 68.3 gm. containing 35.6 weight percent organics and non-detectable sulfate impurity. An analysis of this liquor is presented in Table 4.

TABLE 4

| COMPONENT | MOLED % (EXCLUDE WATER) |
|---|---|
| Cyclic PE formal | 45.3 |
| PE | 20.0 |
| Di-PE | 10.0 |
| Di-cyclic PE formal | 0.3 |
| Linear PE formal | 0.4 |
| Other orgnaics* | 24.0 |

*Higher poly PE and Poly PE formal.

The yields per pass of this example is summarized in Table 5:

TABLE 5

| PRODUCT | YIELD PER PASS (%) |
|---|---|
| Sodium formate | 21 to 25 |
| Methyl formate | 92.7 |
| Organics (PE, etc.) | 47.0 (solids) |
|  | 21.0 (aqueous) |
| Sodium sulfate | 81.0 |

I claim:

1. A process for treating and recovering components from aldol-condensation polyol waste liquor containing sodium formate, water, polyol, and organic by-products comprising:

B. Adding, while maintaining the temperature below about 30° C, a stoichiometric excess of methanol and sulfuric acid, based on the sodium formate content, to the mother liquir from Step A, to form a reaction mixture which is capable of forming methyl formate when heated to 30°–100° C;

C. distilling the mixture of Step B at about 30° to 100° C. and recovering methyl formate as a substantially pure liquid;

D. introducing sodium hydroxide to the bottom residue of Step C to increase the pH to about 6.5 to 7.0;

E. cooling to below about 25° C. so as to precipitate $Na_2SO_4 \cdot 10H_2O$, polyol and organics;

F. adding water to the solid product of Step E at about 30° to 40° C. so as to separate sodium sulfate solution from solid polyol and organics; and G. cooling the sodium sulfate solution from Step F to precipitate substantially pure $Na_2SO_4 \cdot 10H_2O$.

2. The process of claim 1 wherein said substantially pure polyol and organics is technical pentaerithritol.